United States Patent [19]
Hiramoto et al.

[11] Patent Number: 5,801,143
[45] Date of Patent: Sep. 1, 1998

[54] CYCLIC DEPSIPEPTIDES USEFUL FOR TREATMENT OF HYPERLIPEMIA

[75] Inventors: Shigeru Hiramoto; Yukio Saito; Shigeo Hatanaka; Akiko Shingai, all of Saitama-ken, Japan

[73] Assignee: Nisshin Flour Milling Co., Ltd., Tokyo, Japan

[21] Appl. No.: 737,599

[22] PCT Filed: May 25, 1995

[86] PCT No.: PCT/JP95/01003

§ 371 Date: Nov. 25, 1996

§ 102(e) Date: Nov. 25, 1996

[87] PCT Pub. No.: WO95/32990

PCT Pub. Date: Dec. 7, 1995

[30] Foreign Application Priority Data

May 26, 1994 [JP] Japan .................. 6-113023

[51] Int. Cl.[6] .................. C07K 11/00; C07K 7/00; A61K 38/08; A61K 38/15
[52] U.S. Cl. .................. 514/9; 514/11; 530/317; 530/321; 530/359; 435/252.1
[58] Field of Search .................. 514/9, 11; 530/317, 530/321, 324, 359; 435/839, 252.1

[56] References Cited

U.S. PATENT DOCUMENTS 4,891,220  1/1990  Donzis .................. 424/88

FOREIGN PATENT DOCUMENTS

WO 93 17701  9/1993  WIPO.

OTHER PUBLICATIONS

Peptide Chemistry 1994, Protein Research Foundation, No. 32nd, pp. 33–36, 1995, XP 000653596, Takeshi Ohshima, et al., "A New Endothelin Antagonist Lipopetide Isolated from the Strain of *Bacillus subtilis*".

*Primary Examiner*—Stephen Walsh
*Assistant Examiner*—Michael D. Pak
*Attorney, Agent, or Firm*—Oblon, Spivak, McClelland, Maier & Neustadt, P.C.

[57] ABSTRACT

A cyclic depsipeptide having the general formula (I)

(wherein n is an integer of 5–15) or a pharmacologically acceptable salt thereof. The present compound can be prepared by cultivation of a cyclic depsipeptide-producing microorganism belonging to the genus of Bacillus. The present compounds are useful as a therapeutic agent for hyperlipemia, an agent for inhibiting the secretion of lipids or an agent for inhibiting the production of apolipoprotein B.

8 Claims, 3 Drawing Sheets

CYCLIC DEPSIPEPTIDES USEFUL FOR TREATMENT OF HYPERLIPEMIA

This application is a 371 of PCT/JP95/01003 filed on May 25, 1995, and claims priority from Japanese Patent Application 6/113023 filed on May 26, 1994.

TECHNICAL FIELD

This invention relates to a cyclic depsipeptide which has an inhibitory activity on the secretion of lipids and an inhibitory activity on the production of apolipoprotein B and can be utilized as a therapeutic agent for hyperlipemia, a process for producing the same and a use of the same.

BACKGROUND ART

As a therapeutic agent for hyperlipemia, several compounds have been already put into practical use. In particular, it has been reported that an HMG-COA reductase inhibitor such as pravastatin or lovastatin exhibits a remarkable lowering activity of cholesterol and it can be said that the therapy of hypercholesterolemia has been rapidly progressing since the development of such medicines. However, such medicines could not lower a triglyceride level in blood.

On the other hand, as the medicines to lower both a cholesterol level and a triglyceride level, there have been put into practical use clofibrate type medicines and pharmaceutical preparations of nicotinic acid; however, nicotinic acid may develop at a high frequency side-effects such as itching, feverish feeling, rash etc., while clofibrate type medicines have presented the problem of side-effects such as easier formation of gallstone, muscular disorders, hepatic dysfunctions, gastrointestinal disorders, etc. There has been also presented the problem of a considerably higher dose, a dose of niacin as a pharmaceutical preparation of nicotinic acid being 2-3 g and aluminum clofibrate being 1.5 g.

DISCLOSURE OF INVENTION

The subject of this invention is to provide a compound which can far more strongly lower both plasma cholesterol and plasma triglyceride levels as compared with the prior art medicines in order to accomplish the treatment and prevention of hyperlipemia effectively.

Since a greater part of cholesterol and triglyceride in plasma is synthesized in and secreted from liver, it is expectable that a substance capable of inhibiting the secretion of both cholesterol and triglyceride in hepatic cells would be a therapeutic agent for hyperlipemia which can lower both of plasma cholesterol and triglyceride levels. The present inventors have used Hep G2 cells as the model cell for hepatocytes and investigated metabolites produced by microorganisms seeking for the compound which may inhibit the secretion of both cholesterol and triglyceride, and, as a result, found out the active ingredients in a cultured broth of a certain bacteria, which are those compounds having a cyclic depsipeptide structure. These depsipeptides have been isolated and purified from the cultured broth and then proven that they are new compounds. As a result of further studies, it has been confirmed that these cyclic depsipeptides can inhibit the production of apolipoprotein B in hepatic cells or the like, which is the main constitutive protein of very low density lipoprotein (VLDL) regarded as the cause of arteriosclerosis, and can selectively inhibit the secretion of lipids without preventing the synthesis of other proteins such as albumin and others in hepatic cells, upon which this invention has been completed.

According to this invention, there is provided a cyclic depsipeptide represented by the following structural formula (I)

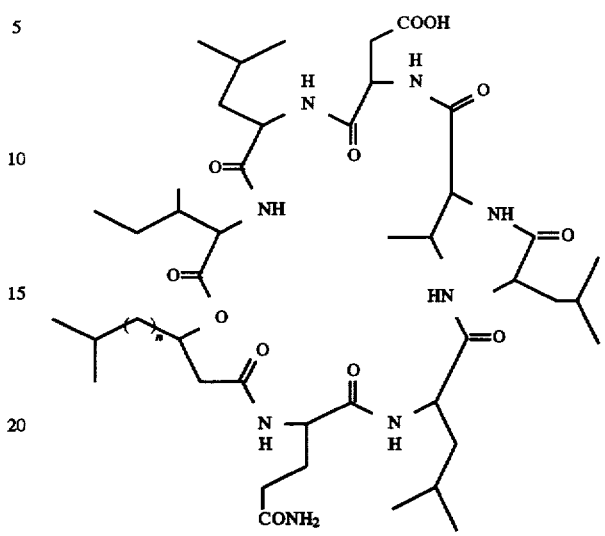

(wherein n represents an integer of 5-15) and a pharmacologically acceptable salt thereof. Preferable are the compounds of the above formula wherein n is an integer of 6-12 and particularly preferable are those compounds wherein n is an integer of 7, 8, 9 or 10.

According to this invention, there is also provided a process for the production of such a cyclic depsipeptide which comprises cultivating a microorganism belonging to the genus of Bacillus and capable of producing the above-mentioned novel cyclic depsipeptide and recovering the cyclic depsipeptide from the cultured broth.

According to this invention, there is further provided a pharmaceutical composition which comprises said cyclic depsipeptide or a pharmacologically acceptable salt thereof, in particular, a therapeutic agent for hyperlipemia, an agent for inhibiting lipid secretion or an agent for inhibiting the production of apolipoprotein B.

The microorganisms which may be used for the production of the cyclic depsipeptide of this invention may be any of those which belong to the genus of Bacillus and produce the present cyclic depsipeptides. For instance, Bacillus sp. No. 4691 strain, separated from a soil sample collected in Otaru-city, Hokkaido is available one. Mycological properties of the No. 4691 strain are as recited below:

1. Morphological properties

Gram-staining Positive

Size 0.7–1.2×1.5–2.5 μm

Morphotype Bacillus

Motility Non-motile

Spores Found, shape: elliptical or cylindrical dominant position: central

2. Cultural properties

1) Growth on nutrient agar medium

Form of colony Irregular on periphery (R form), wholly round

Color Milk white to pale brown

Luster Opaque

Diffusible pigments Not found

2) Nutrient broth

Precipitation of mycelia Not found

Intermediate portion Not turbid
Surface Pellicle found
3) Other properties
Boiling for 30 minutes Resistant
DHL agar medium No growth
Desoxycholate agar medium No growth
4) Gelatin stab culture
Gelatin liquefaction Not found
5) Reaction in litmus milk
Coagulation and peptonization Observed; slightly alkaline pH
3. Physiological properties
They are shown in Table 1 wherein positive is indicated by "+" and negative is indicated by "−".

TABLE 1

| Gram staining | + | O-F test | | Gas |
|---|---|---|---|---|
| Nitrate reduction | + | Glucose | − | − |
| | | Control | − | − |
| Denitrification | + | Formation of acid and gas from saccharide | Acid | Gas |
| MR test | − | L-Arabinose | + | − |
| VP test | + | D-Xylose | − | − |
| Indole formation | − | D-Glucose | + | − |
| $H_2S$ formation | − | D-Mannose | + | − |
| Starch hydrolysis | + | D-Fructose | + | − |
| Utilization of citric acid | + | D-Galactose | + | − |
| | | Maltose | + | − |
| Inorganic nitrogen source | | Sucrose | + | − |
| Nitrate | − | Lactose | − | − |
| Ammonium salt | + | Trehalose | + | − |
| Pigment formation | − | D-Sorbitol | − | − |
| Urease | − | D-Mannitol | + | − |
| Oxydase | + | Inositol | − | − |
| Catalase | + | Glycerol | + | − |
| Growth range | | Starch | + | − |
| Temp. Max · Min | 15–55° C. | Control | − | − |
| pH Optimum | 6.0–8.0 | Resistance to sodium chloride | 0–12% | |
| Max · Min | 5.0–10.0 | Hemolysis | − | |
| Behavior to $O_2$ | Aerobic | Decomposition of Arginine | + | |
| | | Decarboxylation of lysine | − | |
| | | Decarboxylation of ornithine | − | |
| | | Utilization of malonic acid | + | |
| | | Decomposition of aesculin | + | |

4. Chemical taxonomical properties
1) Base composition of DNA (GC content)
50–51%
2) Diaminopimelic acid in the hydrolyzate of a whole cell pellet is of meso type.

In view of the characteristics as stated above, particularly, the results from morphological observation and chemical analysis, the present strain has been considered to belong to the genus of Bacillus. Accordingly, the present strain has been named Bacillus sp. No. 4691. The No. 4691 strain was applied for deposition in the National Institute of Bioscience and Human-Technology, Agency of Industrial Science and Technology, Ministry of International Trade and Industry and then accepted with the accession number of FERM P-14282 on Apr. 20, 1994. Thereafter, it was applied to be transferred to international deposition and internationally deposited with the accession number of FERM BP-5101 on May 15, 1995.

The medium which may be used for the cultivation according to this invention may be any medium provided that it contains optional nutritive sources which may be utilized by the microorganism capable of producing the present cyclic depsipeptide. As carbon sources, there may be used, for example, glycerol, glucose, maltose, sucrose, dextrin, starch, oils and fats and the like. As nitrogen sources, there may be used, for example, organic materials such as soybean meal, meat extract, peptone, dry yeast, yeast extract, corn steep liquor and the like and inorganic salts such as ammonium nitrate, ammonium chloride and the like. And, if necessary, there may be also added inorganic salts such as common salt, potassium chloride, calcium carbonate, phosphates, heavy metal salts and the like. In order to prevent foaming during the fermentation, suitable antifoamings such as silicone, soybean oil and the like may be optionally added in a conventional manner. As the cultivation procedure, there may be used stationary culture, shaken culture, culture with aeration-agitation and others. Cultivation temperature may be suitably 20°–50° C., preferably 25°–40° C. The maximum production of the present physiologically active substance will be obtained in 2–4 days according to either shaken culture or culture with aeration-agitation.

The present cyclic depsipeptide thus produced is mainly present in cell pellets and then it may be desirable for recovery of the said substance to start a purification procedure from the cell pellets obtained by centrifugation or filtration of the cultured broth. For purification, there may be applied purification procedures usually applied for recovery of hydrophobic substances from the cell pellets of a microorganism. More specifically, the cell pellets are extracted with a water-miscible organic solvent such as methanol, ethanol, acetone and the like while stirring to obtain the extract. Then, the organic solvent is distilled off from the extract followed by extraction with a water-immiscible organic solvent such as ethyl acetate. The organic solvent to be used for the extraction may include esters such as ethyl acetate or butyl acetate, halogenated hydrocarbons such as chloroform or methylene chloride, alcohols such as n-butanol or isobutanol.

The extract thus obtained is washed with brine and concentrated to give a crude powder. This powder is subjected to silica gel column chromatography. As the developing solvent, there may be used, for example, a mixed solvent system such as chloroform-methanol or hexane-ethyl acetate, and the desired product may be eluated separately from other contaminants by gradually increasing the ratio of the polar solvent such as methanol or ethyl acetate in the mixed solvent system.

The so-eluted fraction which contains the present cyclic depsipeptide may be further purified by a preparative thin layer chromatography or high performance liquid chromatography (HPLC) and the like to eventually afford the present cyclic depsipeptide.

The present cyclic depsipeptide may form a pharmacologically acceptable salt such as a metal salt, e.g. sodium, potassium or calcium salt, an ammonium salt or a salt with an organic amine such as triethylamine salt and the like according to a method well-known per se.

The present cyclic depsipeptide or a pharmacologically acceptable salt thereof may be formed to pharmaceutical preparations in various dosage forms. More specifically, the preparations may be orally administered in the form of tablets, sugar-coated tablets, hard capsules, soft capsules, granules, powders and liquids such as solutions, emulsions or suspensions. In the case of parenteral administartion, they may be administered in the form of injections or suppositories.

In preparing the pharmaceutical preparations, there may be added additives conventionally used for making pharmaceutical preparations such as excipients, stabilizers, preservatives, solubilizers, wetting agents, emulsifiers, lubricants, sweetening agents, coloring agents, flavors, thickening agents, buffers, antioxidants and the like.

As the additives, there may be mentioned, for example, starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropyl-methylcellulose and the like.

When the present compound is to be used in the form of liquids or injections, the active ingredient may be used in the form of a solution or suspension thereof in a conventional diluent. The diluent may include physiological saline, Ringer's solution, an aqueous solution of glucose, alcohols, aliphatic acid esters, glycols, glycerol aliphatic glycerides, oil sources derived from vegetables and animals, paraffins and the like.

These pharmaceutical preparations can be prepared according to a conventional method.

A usual clinical dose to be applied may be in the range of 0.5–5000 mg for an adult per day when administered orally. More preferably, it may be applied in the range of 5–500 mg.

EXAMPLE

Example 1

Production of the present cyclic depsipeptides

Figure 1:
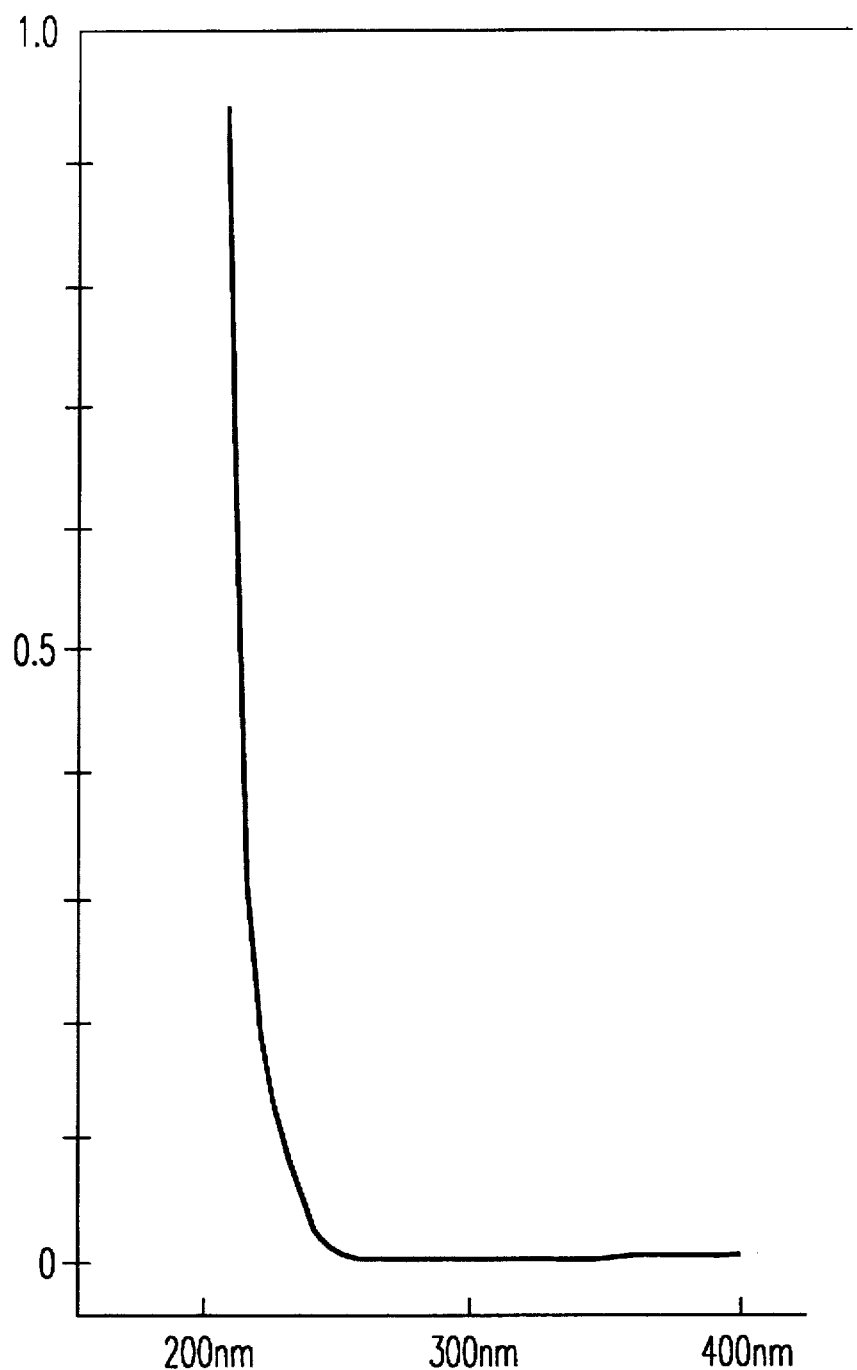
FIG. 1 shows an ultraviolet absorption spectrum of the present cyclic depsipeptide (Compound 1) wherein absorbance is plotted on the ordinate and wavelength (nm) is plotted on the abscissa.

A liquid medium containing 1.0% soluble starch, 1.0% backstrap molasses, 1.0% polypeptone, 1.0% meat extract was poured in 100 ml portions into 500 ml-volume Erlenmeyer flasks, which were then sterilized at 120° C. for 20 minutes in a conventional manner. To the medium was inoculated Bacillus sp. No. 4691 strain previously cultured on an agar slant medium and shaken culture was effected at 28° C. for 48 hours (220 rpm) to produce a seed cultured broth. To 100 ml of a liquid medium containing 2.5% soluble starch, 1.5% soybean meal, 0.2% dry yeast, 0.4% calcium carbonate was inoculated 2 ml of the seed cultured broth and shaken culture was effected at 220 rpm at 28° C. for 3 days. The cultured broth (15 liters) was centrifuged to collect the cell pellet. To the cell pellet were added 5 liters of methanol and, after stirring well, the mixture was allowed to stand for 18 hours. The extract was filtered and the methanol was distilled off under reduced pressure from the filtrate thus obtained. The resulting aqueous solution was adjusted to pH 5 by the addition of 2N hydrochloric acid. The aqueous solution was extracted three times with 1 L of ethyl acetate, washed twice with 500 ml of a saturated aqueous solution of sodium chloride and then dried over anhydrous sodium sulfate. The ethyl acetate extract was concentrated to dryness under reduced pressure, dissolved in a small amount of chloroform and mounted onto a column (200 ml) packed with silica gel suspended in chloroform. The column was washed successively with 300 ml of chloroform, and 300 ml each of chloroform-methanol (98:2) and chloroform-methanol (95:5) to remove impurities. Then, the active fraction was eluted from the column with 300 ml of a solvent system of chloroform-methanol (80:20). The active fraction was concentrated to dryness under reduced pressure and then subjected to a preparative thin layer chromatography (support; silica gel glass plate 60F254, 0.50 mm, available from Merck AG), which was then developed with chlroform-methanol (3:1). The active fraction having the Rf value=0.28 was scratched off and eluted with methanol and the eluate was concentrated to dryness under reduced pressure. The residue was dissolved in a small amount of methanol, mounted onto a column (1.6 cm diameter×60 cm height) packed with Sephadex LH20 (available from Pharmacia) and eluted with methanol to obtain 2.5 ml portions of the eluate. The 18th to the 20th fractions were combined and then concentrated to dryness to afford a colorless crystal, which is designated Compound 1.

The 15th to 17th fractions were concentrated to dryness and then subjected to a high performance liquid chromatography [column; Inertsil ODS (inner diameter 20 mm, length 250 mm, available from GL Science), mobile phase; methanol:water:ammonium acetate=95:5:0.1, flow rate; 15 ml/min., detector; UV222 nm] to obtain the peak of a retention time of 15.20 minutes and the peak of a retention time of 18.06 minutes. Each of them was concentrated to dryness and a white powder of Compound 2 and a white powder of Compound 3 were obtained from the fraction of a retention time of 15.20 minutes and that of a retension time of 18.06, respectively. The 21st to 23rd fractions were also similarly concentrated to dryness and subjected to a high performance liquid chromatography (using the same parameters as above) to separate and obtain the peak with a retention time of 25.02 minutes. It was concentrated to dryness to obtain a white crystal of Compound 4.

Physico-chemical properties of the cyclic depsipeptides of this invention are as shown below.

Compound 1

Form: Colorless crystals

Melting point: 155°–157° C.

Mass spectrometry (FABMS): m/z 1057 (M+Na)

Molecular formula: $C_{53}H_{94}N_8O_{12}$

UV spectrum (MeOH) : End absorption (See, FIG. 1)

Figure 2:
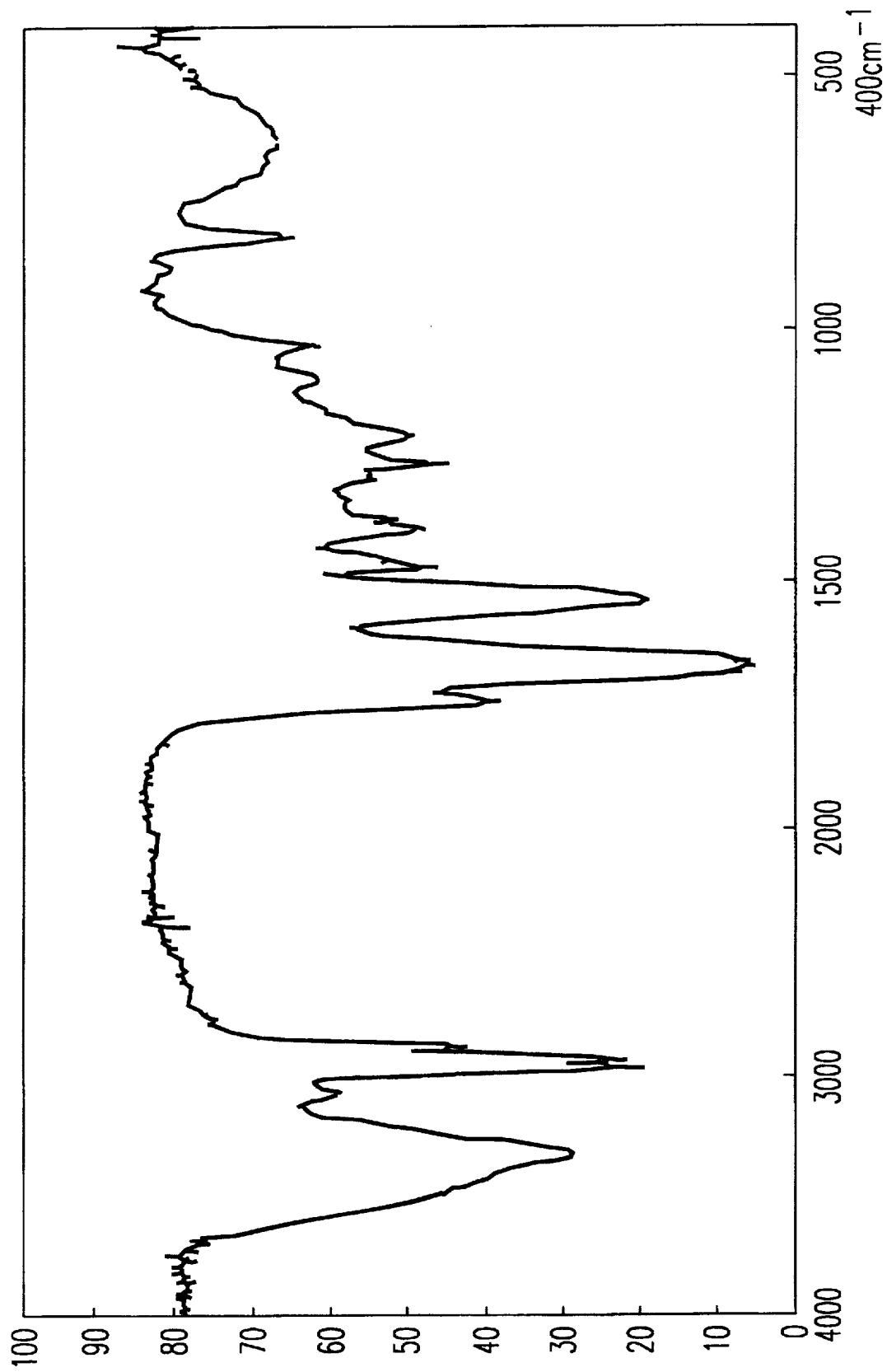
FIG. 2 shows an infrared absorption spectrum of the present cyclic depsipeptide (Compound 1) wherein transmittance (%) is plotted on the ordinate and wavenumber (cm$^{-1}$) is plotted on the abscissa.

IR spectrum (KBr tablet method):
3290, 2958, 2928, 2870, 1750, 1658, 1528, 1468, 1387, 1370, 1260, 1199, 1025, 796 (cm$^{-1}$, See, FIG. 2)

Figure 3:
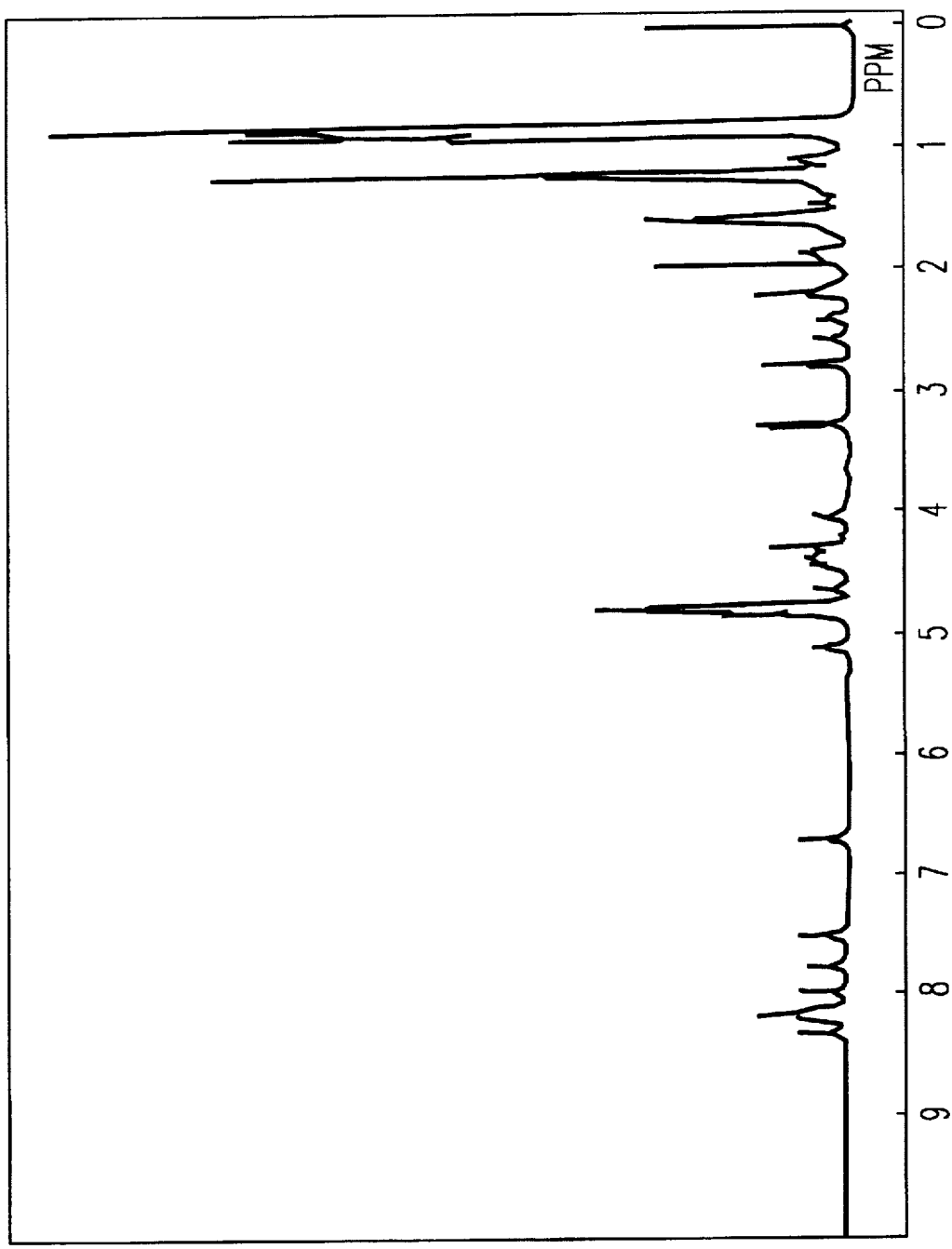
FIG. 3 shows a $^1$H nuclear magnetic resonance spectrum of the present cyclic depsipeptide (Compound 1) wherein chemical shift (ppm; δ) is plotted on the abscissa.

$^1$H Nuclear magnetic resonance spectrum (400 MHz, ppm, multiplicity, Methyl alcohol-d$_3$) 0.79 (6H, d), 0.80 (3H, t), 0.81 (3H, d), 0.82 (3H, d), 0.83 (6H, d), 0.86 (6H, d), 0.87 (3H, d), 0.88 (6H, d), 1.10 (2H, m), 1.20 (16H, m), 1.45 (1H, m), 1.50 (6H, m), 1.54 (2H, m), 1.57 (1H, m), 1.58 (1H, m), 1.63 (1H, m), 1.85 (2H, m), 1.95 (1H, m), 2.12 (1H, m), 2.18 (2H, d-d), 2.35 (1H, d-d), 2.52 (1H, d-d), 2.75 (2H, t), 4.00 (1H, d-d), 4.24 (1H, m), 4.26 (1H, d-d), 4.32 (1H, m), 4.37 (1H, m), 4.42 (1H, m), 4.60(1H, m), 5.05 (1H, m), 6.76 (1H, bs), 7.50 (1H, bs), 7.75 (1H, d), 7.95 (1H, d), 8.08 (1H, d), 8.12 (1H, d), 8.14 (1H, d), 8.19 (1H, d), 8.24 (1H, d) (See, FIG. 3)

$^{13}$C Nuclear magnetic resonance spectrum (100 MHz, ppm, multiplicity, Methyl alcohol-d$_4$) 11.9 (q), 16.1 (q), 18.5 (q), 19.7 (q), 22.2 (q), 22.2 (q), 22.8 (q), 23.1 (q), 23.1 (q), 23.1 (q), 23.4 (q), 23.4 (q), 25.8 (d), 26.0 (d), 26.0 (d), 26.1 (t), 26.4 (t), 28.5 (t), 29.1 (t), 29.1 (d), 30.3 (t), 30.6 (t), 30.6 (t), 30.7 (t), 30.9 (d), 31.0 (t), 32.7 (t), 35.2 (t), 37.4 (t), 38.4 (d), 40.2 (t), 41.2 (t), 41.5 (t), 41.5 (t), 42.0 (t), 52.0 (d), 52.8 (d), 53.4 (d), 53.8 (d), 54.1 (d), 58.3 (d), 61.2 (d), 73.9 (d), 172.2 (s), 172.5 (s), 173.0 (s), 173.3 (s), 173.7 (s), 173.7 (s), 174.8 (s), 175.0 (s), 175.4 (bs), 177.8 (s)

Specific rotation $[\alpha]_D^{29} -11.2$ (c=0.414, MeOH)

Thin layer chromatography (support: Silica gel glass plate 60F254, 0.25 mm, available from Merck AG)

Developing solvent Rf

Chloroform-methanol (3:1) 0.28

Chloroform-methanol-28% aqueous ammonia (10:4:1) 0.52

Compound 2

Form: White powder

Mass spectrometry (FABMS): m/z 1007(MH)*

Molecular formula: $C_{51}H_{90}N_8O_{12}$

UV spectrum (MeOH): End absorption

IR spectrum (KBr tablet method):

3320, 2958, 2928, 1740, 1658, 1520, 1439, 1391, 1202 ($cm^{-1}$)

$^1$H Nuclear magnetic resonance spectrum (400 MHz, ppm, multiplicity, Methyl alcohol-$d_4$) 0.79 (6H, d), 0.80 (3H, t), 0.81 (3H, d), 0.82 (3H, d), 0.83 (6H, d), 0.86 (6H, d), 0.87 (3H, d), 0.88 (6H, d), 1.10 (2H, m), 1.20 (12H, m), 1.45 (1H, m), 1.50–1.65 (11H, m), 1.85 (2H, m), 1.95 (1H, m), 2.12 (1H, m), 2.18 (2H, d-d), 2.35 (1H, d-d), 2.55 (1H, d-d), 2.78 (2H, d), 4.00 (1H, d), 4.24 (1H, d-d), 4.26 (1H, d), 4.32 (1H, d-d), .4.37 (1H, d-d), 4.42 (1H, d-d), 4.60 (1H, d-d), 5.08 (1H, m)

Thin layer chromatography (support: Silica gel glass plate 60F254, 0.25 mm, available from Merck AG)

Developing solvent Rf

Chloroform-methanol (3:1) 0.28

Chloroform-methanol-28% aqueous ammonia (10:4:1) 0.52

High performance liquid chromatography

Column ; Inertsil ODS (available from GL Science)

Mobile phase ; methanol : water : ammonium acetate (97:3:0.1)

Flow rate; 1.0 ml/min., Detector; UV222 nm,

Retention time; 4.38 min.

Compound 3

Form : White powder

Mass spectrometry (FABMS): m/z 1021(MH)$^+$

Molecular formula : $C_{52}H_{92}N_8O_{12}$

UV spectrum (MeOH) : End absorption

IR spectrum (KBr tablet method):

3330, 2958, 2928, 1736, 1652, 1520, 1456, 1389, 1203 ($cm^{-1}$)

$^1$H Nuclear magnetic resonance spectrum (400 MHz, ppm, multiplicity, Methyl alcohol-$d_4$) 0.79 (6H, d), 0.80 (3H, t), 0.81 (3H, d), 0.82 (3H, d), 0.83 (6H, d), 0.86 (6H, d), 0.87 (3H, d), 0.88 (6H, d), 1.10 (2H, m), 1.20 (14H, m), 1.45 (1H, m), 1.50–1.65 (11H, m), 1.85 (2H, m), 1.95 (1H, m), 2.13 (1H, m), 2.18 (2H, d-d), 2.38 (1H, d-d), 2.52 (1H, d-d), 2.68 (1H, d-d), 2.73 (1H, d-d), 4.05 (1H, d), 4.25 (1H, d-d), 4.27(1H, d-d), 4.32 (1H, d-d), 4.35(1H, d-d), 4.42 (1H, d-d), 4.60 (1H, d-d), 5.08 (1H, m)

Thin layer chromatography (support: Silica gel glass plate 60F254, 0.25 mm, available from Merck AG)

Developing solvent Rf

Chloroform-methanol (3:1) 0.28

Chloroform-methanol-28* aqueous ammonia (10:4:1) 0.52

High performance liquid chromatography

Column ; Inertsil ODS (available from GL Science)

Mobile phase ; Methanol : water: ammonium acetate (97:3:0.1)

Flow rate; 1.0 ml/min., Detector; UV222 nm,

Retention time; 4.68 min.

Compound 4

Form : White powder

Mass spectrometry (FABMS): m/z 1049(MH)$^+$

Molecular formula : $C_{54}H_{96}N_8O_{12}$

UV spectrum (MeOH) : End absorption

IR spectrum (KBr tablet method):

3310, 2958, 2928, 1745, 1658, 1525, 1440, 1391, 1202 ($cm^{-1}$)

$^1$H Nuclear magnetic resonance spectrum (400 MHz, ppm, multiplicity, Methyl alcohol-$d_4$) 0.79 (6H, d), 0.80 (3H, t), 0.81 (3H, d), 0.82 (3H, d), 0.83 (6H, d), 0.86 (6H, d), 0.87 (3H, d), 0.88 (6H, d), 1.10 (2H, m), 1.20 (18H, m), 1.45 (1H, m), 1.50–1.65 (11H, m), 1.85 (2H, m), 1.95 (1H, m), 2.12 (1H, m), 2.18 (2H, d-d), 2.35 (1H, d-d), 2.53 (1H, d-d), 2.75 (2H, d), 4.00 (1H, d), 4.24 (1H, d-d), 4.26 (1H, d), 4.32 (1H, d-d), 4.37(1H, d-d), 4.42 (1H, d-d), 4.60 (1H, d-d), 5.04 (1H, m)

Thin layer chromatography (support: Silica gel glass plate 60F254, 0.25 mm, available from Merck AG)

Developing solvent Rf

Chloroform-methanol (3:1) 0.28

Chloroform-methanol-28% aqueous ammonia (10:4:1) 0.52

High performance liquid chromatography

Column ; Inertsil ODS (available from GL Science)

Mobile phase ; Methanol: water: ammonium acetate (97:3:0.1)

Flow rate; 1.0 ml/min., Detector; UV222 nm,

Retention time; 5.40 min.

From the above results, the structures of Compounds 1–4 are as defined below:

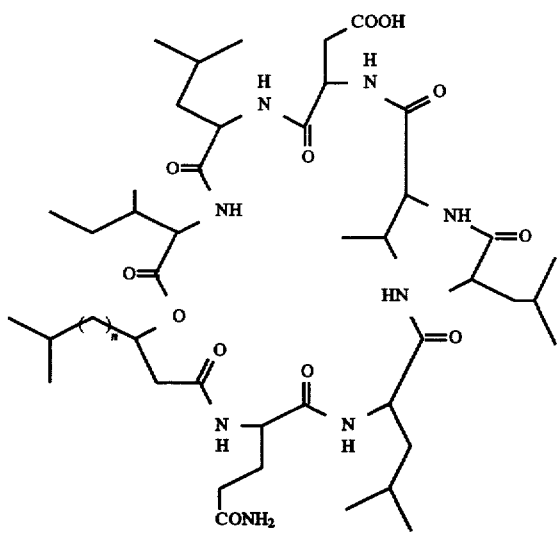

n=7 Compound 2
n=8 Compound 3
n=9 Compound 1
n=10 Compound 4

(Pharmacological activities)

Test Example 1

Inhibitory activity of the present cyclic depsipeptide on cholesterol secretion

Into each of 24-well tissue culture plates were poured in 1 ml portions Hep G2 cells at 1×10⁵ cells/ml [Dulbecco modified Eagle medium containing 10% bovine fetal serum (available from Nissui Seiyaku K.K.; hereafter referred to as D-MEM medium)] and incubated at 37° C. under a mixed gas atmosphere of 5% carbon dioxide and 95% air. After 4 days, the medium was removed and 1 ml of D-MEM medium containing 10% lipoprotein-deficient serum (available from Sigma) and then 10 µl of a methanolic solution of the cyclic depsipeptide were added. After 18 hours, the medium was again exchanged (D-MEM medium containing 10% lipoprotein-deficient serum), 10 µl of a methanolic solutiuon of the cyclic depsipeptide and 3 µCi [1-$^{14}$C]acetic acid were added and then incubation was carried out at 37° C. for further 18 hours. The [$^{14}$C] cholesterol produced in the said medium was determined according to the method disclosed in Biochimica et Biophysica Acta, Vol. 1042, pp. 36–41 (1990).

More specifically, the medium was extracted with chloroform/methanol (2:1) and then the extract was subjected to saponification reaction in 15% potassium hydroxide under the condition of 85° C. and 45 minutes to convert the ester-typed cholesterol to the free-typed cholesterol. The cholesterol was extracted with petroleum ether and subjected to a silica gel thin layer chromatography and developed with hexane/diethyl ether/acetic acid (80:20:1). Spots of cholesterol were scratched away and a radioactivity thereof was measured by means of a liquid scintillation counter and defined as an amount of [$^{14}$C]cholesterol.

On the other hand, measurement was made in the same manner as in Test Example 1, except that methanol was used instead of the methanolic solution of the cyclic depsipeptide, to prepare a control group. Further, a relative amount of cholesterol was calculated, defining as 100 an amount of the control [$^{14}$C]cholesterol.

Effects of the present cyclic depsipeptides at various concentrations on cholesterol secretion are shown in Table 2.

TABLE 2

Effects of the present cyclic depsipeptides on cholesterol secretion

| Compound | Conc. (µg/ml) | Relative cholesterol amount (%) |
|---|---|---|
| 1 | 0.1 | 83 |
| 1 | 0.3 | 73 |
| 1 | 0.9 | 47 |
| 1 | 2.7 | 28 |
| 1 | 8.1 | 23 |
| 2 | 8.1 | 41 |
| 3 | 8.1 | 44 |
| 4 | 8.1 | 17 |

Test Example 2

Inhibitory activity of the present cyclic depsipeptides on triglyceride secretion Hep G2 cells at 1×10⁵ cells/ml (D-MEM medium containing 10% fetal bovine serum) were poured in 1 ml portions into 24-well tissue culture plates and incubation was carried out at 37° C. under the atmosphere of a mixed gas of 5% carbon dioxide and 95% air. After 4 days, the medium was removed, 1 ml of the D-MEM medium containing 10% lipoprotein-defective serum (available from Sigma) was added and further 10 µl of a solution of the new cyclic depsipeptide in methanol was added. After 18 hours, the medium was again replaced (the D-MEM medium containing 10% lipoprotein-deficient serum) and then 10 µl of a solution of the new cyclic depsipeptide in methanol and [2-$^3$H]glycerol 3 µCi were added. Then, incubation was carried out at 37° C. for 18 hours. The [$^3$H]triglyceride produced in the medium was assayed according to the method disclosed in Biochimica et Biophysica Acta, Vol. 1170, pp. 32–37 (1993).

More specifically, the medium was extracted with hexane/isopropanol (3:2), and the extract was subjected to a silica gel thin layer chromatography and developed with hexane/diethyl ether/acetic acid (90:10:1). Spots of the triglyceride were scratched away and determined for radioactivity by means of a liquid scintillation counter and the radioactivity was defined as an amount of the [$^3$H]triglyceride.

Controls were also prepared by using methanol instead of the solution of the cyclic depsipeptide in methanol used in Test Example 2 and performing the assay in the same manner as the Test Example. Then, a relative triglyceride amount was determined, defining the [$^3$H]triglyceride amount in controls as 100.

Influence by the present cyclic depsipeptide at various concentrations on triglyceride secretion is shown in Table 3.

TABLE 3

Effects of the present cyclic depsipeptides on triglyceride secretion

| Compound | Conc. (µg/ml) | Relative triglyceride amount (%) |
|---|---|---|
| 1 | 2.7 | 84 |
| 1 | 8.1 | 51 |
| 2 | 8.1 | 77 |
| 3 | 8.1 | 86 |
| 4 | 8.1 | 75 |

It has been proven from the results of Tables 2 and 3 that the present cyclic depsipeptide can inhibit in concentration-dependence the secretion of cholesterol and triglyceride in hepatic cells.

Test Example 3

Influence of the present cyclic depsipeptide on the production of apolipoprotein B and albumin in Hep G2 cells Hep G2 cells at 1×10⁵ cells/ml (D-MEM medium containing 10% fetal bovine serum) were poured in 1 ml portions into 24-well tissue culture plates and incubation was carried out at 37° C. under the atmosphere of a mixed gas of 5% carbon dioxide and 95% air. After 4 days, the medium was removed, 1 ml of the D-MEM medium containing 10% lipoprotein-defective serum (available from Sigma) was added and further 10 μl of a solution of the cyclic depsipeptide in methanol was added. After 18 hours, the medium was again replaced (the D-MEM medium containing 10%

After washing three times with 300 μl of PBS, 300 μl of the blocking solution was added and the mixture was allowed to stand at 37° C. for 2 hours. Again, it was washed three times with 300 μl of PBS, 50 μl of a sample liquid [Hep G2 medium diluted to 3.3 times with a 10% immunoblocking agent derived from milk protein (Block Ace; avaialable from Dainippon Pharmaceutical Co., Ltd.)] was added and the mixture was allowed to stand at room temperature for 2 hours. After washing three times with 300 μl of PBS-T, 50 μl of a 0.5% solution of sheep anti-human apolipoprotein B labeled with peroxidase (available from Bindingsite) (10% Block Ace) was added and the mixture was allowed to stand at room temperature for 2 hours. After washing 5 times with 300 μl of PBS-T, 100 μl of a coloring solution (1 ml of 0.1M potassium citrate pH 4.5, 0.4 μl of 30% hydrogen peroxide and 1 mg of orthophenylene diamine) was added and allowed to stand as such for 2 min. Reaction was stopped by the addition of 100 μl of 2N sulfuric acid and the difference between absorbance at 490 nm and that at 650 nm was determined and defined as absorbance of apolipoprotein B. Following the same procedure and determination as in Test Example 3 except that methanol was used instead of the methanolic solution of cyclic depsipeptide, controls were prepared. Using the calibration curve made by using low density lipoprotein (available from Sigma) as a standard, an absolute amount of apolipoprotein B was determined and a relative amount of apolipoprotein B in lipoprotein-deficient serum) and then 10 μl of a solution of the cyclic depsipeptide in methanol was added. Then, incubation was carried out at 37° C. for 18 hours. The apolipoprotein B and albumin produced in the medium were assayed according to an enzyme immunoassay method. Assay of each protein will be explained in detail below.

1) Assay of apolipoprotein B

The composition of the buffer used in this method will be shown in Table 4, wherein PBS and PBS-T mean a phosphate buffered-saline and a phosphate buffered-saline added with Tween 20, respectively.

TABLE 4

| Composition of Buffer | | |
|---|---|---|
| PBS (pH 7.2) | PBS-T (pH 7.2) | Blocking solution (pH 7.2) |
| KH₂PO₄ 0.2 g | KH₂PO₄ 0.2 g | Block Ace 250 ml |
| Na₂HPO₄.12H₂O 2.9 g | Na₂HPO₄.12H₂O 2.9 g | KH₂PO₄ 0.2 g |
| NaCl 8.0 g | NaCl 8.0 g | Na₂HPO₄.12H₂O 2.9 g |
| KCl 0.2 g | KCl 0.2 g | NaCl 8.0 g |
| | Tween 20 0.5 g | KCl 0.2 g |

*The buffer was prepared to be a total volume of 1000 ml by the addition of distilled water.

Sheep anti-human apolipoprotein B IgG fraction (available from Bindingsite Co., Ltd.) was dissolved in 0.05 M sodium hydrogencarbonate (pH 9.5) so as to be 10 μg/ml. 50 μl of this solution was poured in portions into a Nunkimmunoplate, which was allowed to stand at 4° C. for 16 hours. each sample was expressed in terms of a ratio of the amount of the sample to that of the control×100%.

2) Assay of albumin

Assay was carried out in the same manner as apolipoprotein B, except that sheep anti-human albumin IgG fraction (avaialble from Bindingsite) was used instead of the sheep anti-human apolipoprotein B IgG fraction (available from Bindingsite) and sheep anti-human albumin labeled with peroxidase was used instead of the sheep anti-human apolipoprotein B labeled with peroxidase, while as a sample liquid was added 50 μl of Hep G2 medium diluted to 13.3 times with 10% Block Ace. As a standard for drawing up a calibration curve was used human albumin (available from Sigma). A relative albumin amount of the sample was determined in terms of a ratio (%), defining an absolute amount of albumin of the control as 100.

Influence of the present cyclic depsipeptide on the production of apolipoprotein B and albumin at the respective concentrations are shown in Table 5.

TABLE 5

Influence of the present cyclic depsipeptides on the production of apolipoprotein B and albumin

| Compound | Conc. (μg/ml) | Relative amount of apolipoprotein B (%) | Relative amount of albumin (%) |
|---|---|---|---|
| 1 | 12.5 | 48 | 99 |
| 1 | 25.0 | 24 | 106 |

From the results of Table 5, it has been proven that the cyclic depsipeptide of this invention can selectively inhibit the production of apolipoprotein B in Hep G2 cells without any influence on the production of albumin.

From the above results, it is evident that the cyclic depsipeptide of this invention can strongly inhibit the secretion of cholesterol and triglyceride in Hep G2 cells at a low concentration and further inhibit the production of apolipoprotein B, but not the secretion of other proteins such as albumin and so on. Thus, it is expectable to be utilized as a highly selective and new type of the therapeutic agent for hyperlipemia.

(Preparation Example)

Preparation Example 1 Tablets (each tablet)

| | |
|---|---|
| Compound 1 | 20 mg |
| Magnesium silicate | 20 mg |
| Lactose | 98.5 mg |
| Hydroxypropylcellulose | 7.5 mg |
| Magnesium stearate | 1 mg |
| Hardened vegetable oil | 3 mg |
| Total | 150 mg |

Compound 1, magnesium silicate and lactose were mixed, the mixture was kneaded with an alcoholic solution dissolving hydroxypropylcellulose and then granulated to an adequate particle size, dried and graded. Then, magnesium stearate and hardened vegetable oil were added and mixed to form uniform granules. Then, tablets, each having a diameter of 7.0 mm, a weight of 150 mg and a hardness of 6 kg, were prepared by means of a rotary tablet machine.

13
Preparation Example 2 Granules

| Compound 1 | 10 mg |
|---|---|
| Magnesium oxide | 40 mg |
| Calcium hydrogenphosphate | 38 mg |
| Lactose | 10 mg |
| Hydroxypropylcellulose | 20 mg |

All materials in the above formulation were uniformly mixed except for hydroxypropylcellulose, an alcoholic solution dissolving hydroxypropylcellulose was added and the mixture was kneaded and granulated by means of an extrusion granulation machine and then dried to give granules. The granules were graded and sieved to form granules passing through a 12 mesh screen and remaining on a 48 mesh screen.

Preparation Example 3 Syrups

| Compound 1 | 1.000 g |
|---|---|
| Sucrose | 30.000 g |
| D-Sorbitol 70 w/v% | 25.000 g |
| Ethyl para-hydroxybenzoate | 0.030 g |
| Propyl para-hydroxybenzoate | 0.015 g |
| Flavour | 0.200 g |
| Glycerol | 0.150 g |
| 96% Ethanol | 0.500 g |
| Purified water | ad lib |
| Total volume | 100 ml |

In 60 g of purified water (warm water) were dissolved sucrose, D-sorbitol, methyl para-hydroxybenzoate, propyl para-hydroxybenzoate and Compound 1. After cooling, a solution of glycerol and ethanol dissolving flavour was added. Then, to the mixture was added purified water to make up 100 ml.

Preparation Example 4 Injections

| Compound 1 sodium salt | 10.0 mg |
|---|---|
| Sodium chloride | 81.0 mg |
| Sodium hydrogencarbonate | 8.40 mg |
| Distilled water for injection | ad lib |
| Total volume | 10.0 ml |

Sodium hydrogencarbonate, sodium chloride and Compound 1 sodium salt were dissolved in distilled water to make up a total volume to 10.0 ml.

Preparation Example 5 Suppositories

| Compound 1 | 2 g |
|---|---|
| Polyethylene glycol 4000 | 20 g |
| Glycerol | 78 g |
| Total weight | 100 g |

To Compound 1 was added glycerol to form a solution. Polyethylene glycol 4000 was added to the solution and molten by warming. Then, it was poured into a suppository mold and solidified by cooling to form suppositories, each having a weight of 1.5 g.

Industrial Applicability

The cyclic depsipeptides (I) provided according to this invention are useful as a therapeutic agent for hyperlipemia, in particular, an agent for inhibiting the secretion of lipids and an agent for inhibiting the production of apolipoprotein B. The compounds of this invention may be prepared by cultivation of a microorganism which is capable of producing the said compounds and belongs to the genus of Bacillus.

We claim:

1. A cyclic depsipeptide having the structural formula (I)

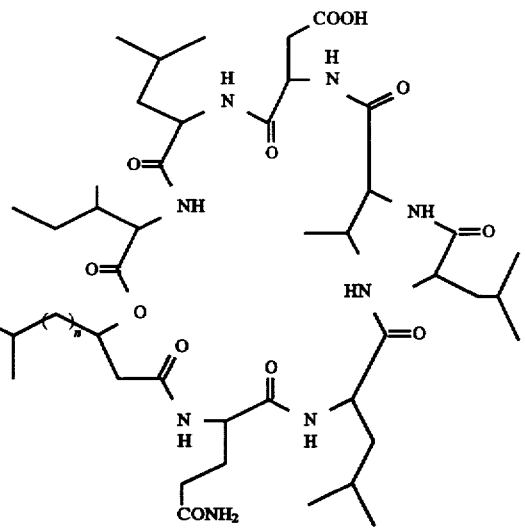

(wherein n is an integer of 5–15) and a pharmacologically acceptable salt thereof.

2. The cyclic depsipeptide of claim 1 and a pharmacologically acceptable salt thereof wherein n is an integer of 6–12.

3. The cyclic depsipeptide of claim 1 and a pharmacologically acceptable salt thereof wherein n is 7, 8, 9 or 10.

4. A process for the preparation of a cyclic depsipeptide which comprises cultivating a microorganism belonging to the genus of Bacillus and capable of producing a cyclic depsipeptide of claim 1 and recovering the cyclic depsipeptide thus produced from a cultured broth.

5. A pharmaceutical composition which comprises a cyclic depsipeptide of claim 1 or a pharmacologically acceptable salt thereof and a pharmacologically acceptable carrier.

6. A method for treating hyperlipemia which comprises administering to a patient in need thereof a cyclic depsipeptide of claim 1 or a pharmacologically acceptable salt thereof.

7. A method for inhibiting the secretion of lipids which comprises administering to a patient in need thereof a cyclic depsipeptide of claim 1 or a pharmacologically acceptable salt thereof.

8. A method for inhibiting the production of apolipoprotein B which comprises administering to a patient in need thereof a cyclic depsipeptide of claim 1 or a pharmacologically acceptable salt thereof.

* * * * *